United States Patent [19]

Horntrich

[11] Patent Number: 4,768,671
[45] Date of Patent: Sep. 6, 1988

[54] COVER FOR WATER CONTAINER OR ORAL RINSING DEVICE

[75] Inventor: Gunter Horntrich, Pforzheim, Fed. Rep. of Germany

[73] Assignee: Blendax-Werke, R. Schneider GmbH & Company, Fed. Rep. of Germany

[21] Appl. No.: 138,858

[22] Filed: Dec. 29, 1987

[51] Int. Cl.$^4$ .............................................. B65D 49/02
[52] U.S. Cl. ..................................... 220/18; 220/263
[58] Field of Search ................ 220/18, 1 T, 318, 262, 220/263; 248/133, 128, 143, DIG. 7; 232/1 E, 65

[56] References Cited

U.S. PATENT DOCUMENTS

| 3,885,700 | 5/1975 | Allard | 220/18 |
| 3,935,964 | 2/1976 | Saxe | 220/18 |
| 4,300,696 | 11/1981 | Bryce | 220/18 |

Primary Examiner—George T. Hall
Attorney, Agent, or Firm—Connolly and Hutz

[57] ABSTRACT

A stationary hinged covering device for a removably arranged container of an oral rinsing device comprises an upright support with a horizontally disposed stationary carrier secured to the support. A container cover has a front portion and a slightly heavier rear portion with a hinge pivotally connecting the container cover to the stationary carrier at a point between the front and rear portions of the cover. The cover has a rearwardly and downwardly extending flap at the rear portion thereof arranged to engage the rim of a container when positioned under the cover. When the container is removed the front portion of the cover swings in an upward direction about the hinge while the rear portion swings in a downward direction. When the container is positioned directly under the cover the cover is horizontally disposed.

2 Claims, 2 Drawing Sheets

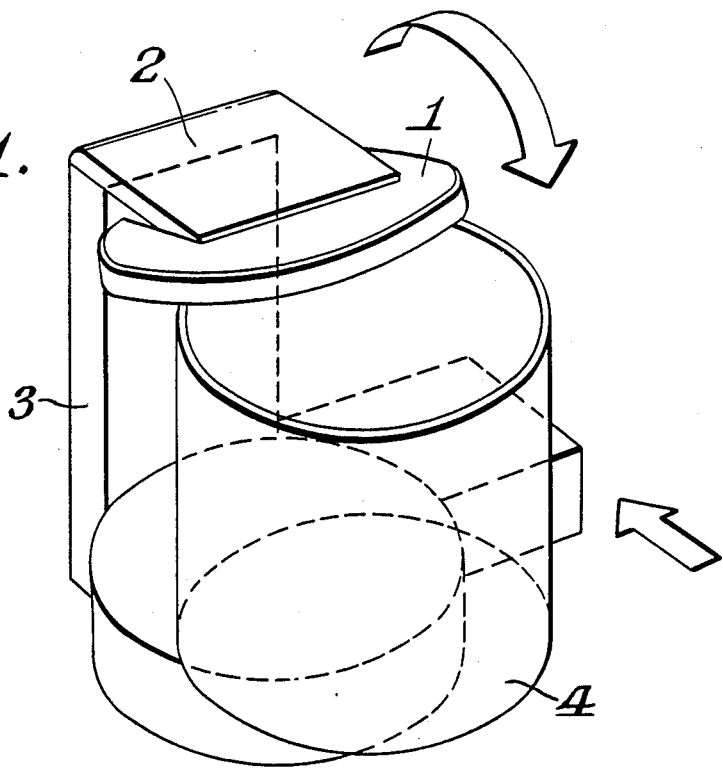
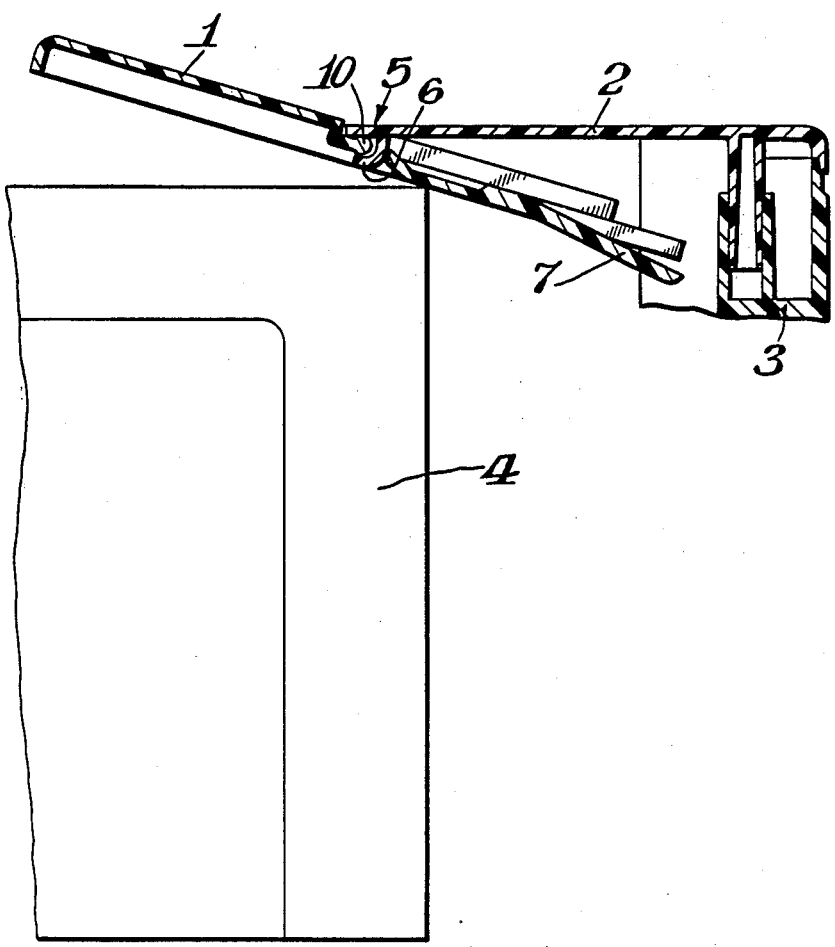

COVER FOR WATER CONTAINER OR ORAL RINSING DEVICE

BACKGROUND OF THE INVENTION

The present invention relates to a novel covering device for the water container of an oral rinsing device having improved use properties.

The reservoir for the liquid of an oral rinsing device is generally arranged in either a fixed or movable condition. The fixed arrangement has a serious disadvantage in that the entire oral rinsing device must be taken to a water source for the purpose of refiling the container. As a result, movably arranged liquid containers are generally preferred. These liquid containers are in most cases equipped with a removable cover to prevent contamination of the water provided for oral rinsing.

Since removing and replacing a loose cover has disadvantages, in particular, cumbersome handling, covering devices permanently installed on the liquid container often have openings for the purpose of refilling with the rinsing water.

Covering devices having such filling openings have the disadvantage, however, that impurities are deposited in the water reservoir, in particular, when the oral rinsing device is not in use.

SUMMARY OF THE INVENTION

Accordingly, it is an objective of the present invention to provide a covering device for the water container of an oral rinsing device which allows for simple handling of the container but at the same time guarantees complete covering thereof.

A fixed, hinged-on covering device for a removably arranged water container of an oral rinsing device is arranged in such a way that it consists of two movably interconnected parts. Specifically the cover has a front and a rear part and a horizontal stationary carrier part. The cover is held on the horizontal carrier by a hinging device arranged in the center of the cover and pivoting about a lateral axis. The carrier is fastened to a vertically arranged holding part which is connected to the base of the oral rinsing device. The rear part of the cover is reinforced with material so that it rests on the rim of the water container when not in use and the front part of the cover pivots in an upward direction when the water container is removed.

As a result of this combination of characteristics, the water container can be readily removed whereby the front part of the covering device pivots upwardly and stops at an angle of about 15° to 40°. The rear, material-reinforced part pivots downwardly since it no longer rests on the rim of the water container.

When the water container is returned to the covering device and pushed in, its rim slides along the bottom face of the cover and presses the cover back to its horizontal position.

A spacer is preferably arranged at the rear, material-reinforced part of the covering device between such part and the water container. The spacer rests on the rim of the water container and as a result produces a gap between between container and cover.

This refinement of the covering device provides an essential improvement over known covering devices.

BRIEF DESCRIPTION OF THE DRAWING

Novel features and advantages of the present invention will become apparent to those of oridnary skill in the art from a reading of the following detailed description in conjunction with the accompanying drawing wherein similar references refer to similar parts and in which:

FIG. 1 is a perspective view of a covering device and water container of an oral rinsing device, according to the present invention;

FIG. 4 is a sectional view similar to FIG. 3 but showing the water container being removed (or inserted).

DETAILED DESCRIPTION OF THE INVENTION

Figure 2:
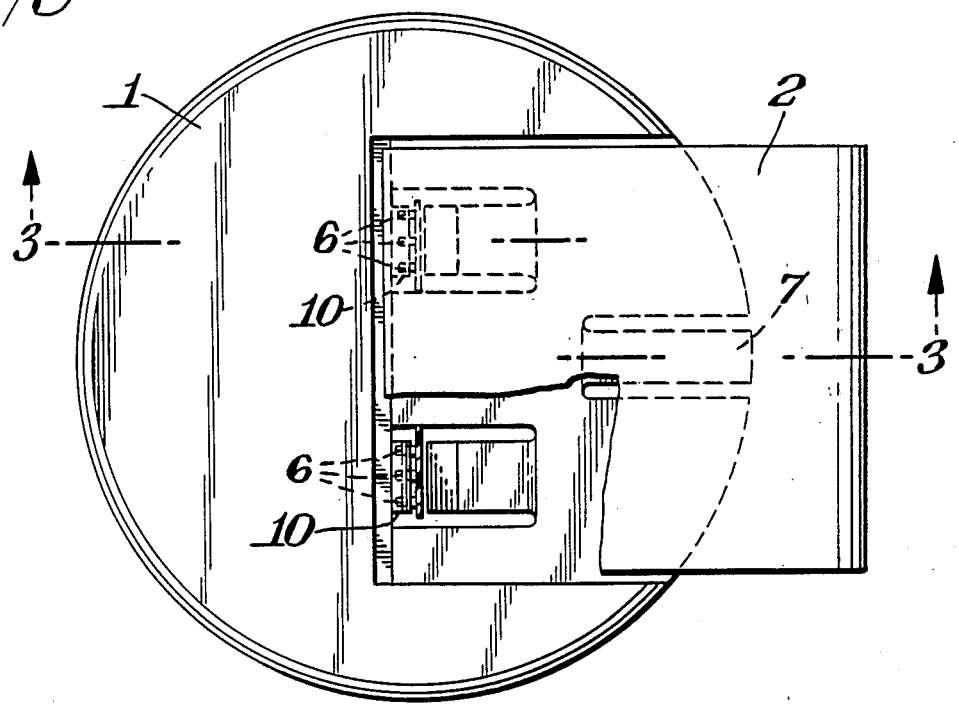
FIG. 2 is a top plan view of the oral rinsing device of FIG. 1 with portions broken away to show detail.
Figure 3:
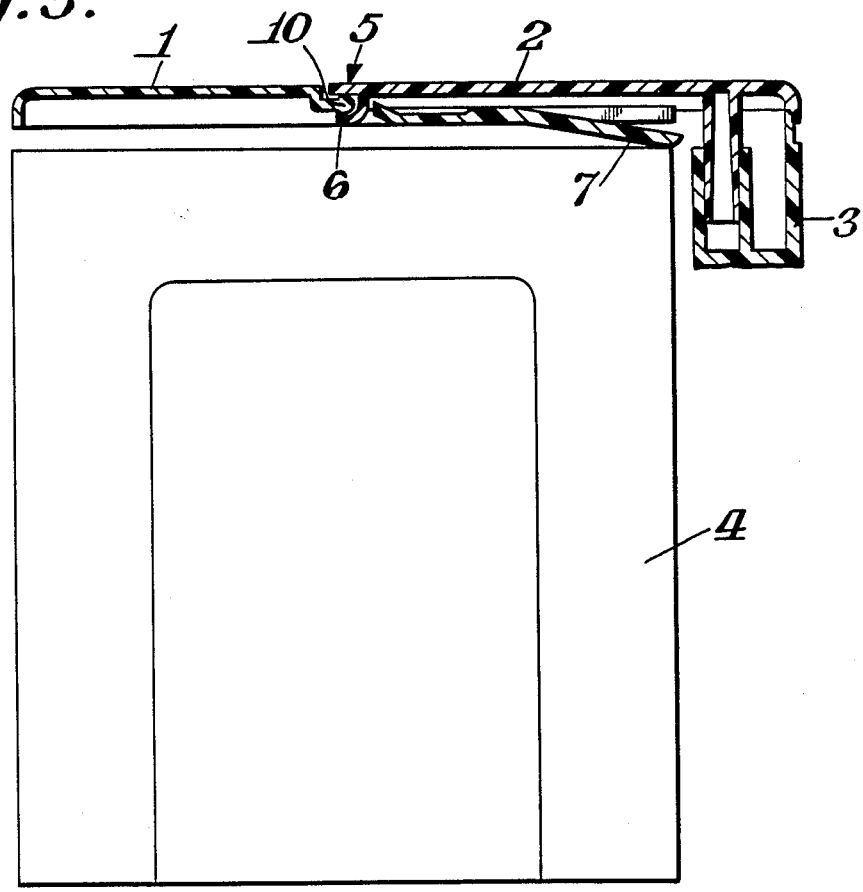
FIG. 3 is a sectional view taken along line 3—3 of FIG. 2.

Referring in more particularity to the drawing, FIGS. 1-4 illustrate a cover 1 for a water container 4 of an oral rinsing device. The device includes an upright support 3 with a horizontally disposed stationary carrier 2 secured to the support. The free end of the stationary carrier 2 includes spaced apart arcuate fingers 6, downwardly extending from the underside of the carrier 2.

Container cover 1 has front and rear portions with spaced apart integral hinge pins 10 between the front end rear portions of the cover. Hinge pins 10 cooperate with the arcuate fingers 6 of the stationary carrier to form a hinge connection 5 between the cover and the carrier.

Container cover 1 includes a downwardly and rearwardly extending flap 7 at the rear portion thereof. As shown best in FIGS. 3 and 4 flap 7 engages the rim of the container 4 when the container is positioned beneath the cover. Flap 7 also functions to provide clearance between the front portion of cover and container 4. Without the flap troublesome interference would exist between the cover and container thereby hampering removal and reinsertion of the container.

The portion of the container cover rearward of the hinge connection 5 is slightly heavier than the cover portion forward of the hinge 5. As such, when container 4 is withdrawn, cover 1 swings upwardly out of the way, as shown in FIG. 4. Conversely, when the container is returned to the oral rinsing device the container rim engages the underside of the rear portion of the cover and the flap 7 thereby causing the cover to downwardly pivot about hinge 5 to the position illustrated in FIG. 3.

The various components described above may be manufactured of thermoplastic materials by techniques known in the art. Other materials are equally suitable.

What is claimed is:

1. A stationary hinged covering device for a removably arranged container of an oral rinsing device comprising an upright support, a horizontally disposed stationary carrier secured to the support, a container cover having a front portion and a slightly heavier rear portion, hinge means pivotally connecting the container cover to the stationary carrier at a point between the front and rear portions of the cover, and the cover having a downwardly and rearwardly extending flap at the rear portion thereof arranged to engage the rim of a container when positioned beneath the cover whereby the front portion of the cover pivots in an upward direction when the container is removed.

2. A stationary hinged covering device as in claim 1 wherein the hinge means includes a pair of spaced apart hinges.

* * * * *